(12) United States Patent
Wu

(10) Patent No.: US 8,781,182 B2
(45) Date of Patent: Jul. 15, 2014

(54) MULTI-PASS EDGE DETECTION OF COLLIMATOR BLADES IN DIGITAL RADIOGRAPHY IMAGES

(75) Inventor: Nailong Wu, Woodbridge (CA)

(73) Assignee: Varian Medical Systems, Inc., Palo Alto, CA (US)

( * ) Notice: Subject to any disclaimer, the term of this patent is extended or adjusted under 35 U.S.C. 154(b) by 403 days.

(21) Appl. No.: 12/416,666

(22) Filed: Apr. 1, 2009

(65) Prior Publication Data

US 2009/0245466 A1    Oct. 1, 2009

Related U.S. Application Data

(60) Provisional application No. 61/041,266, filed on Apr. 1, 2008.

(51) Int. Cl.
*G06K 9/00* (2006.01)
*G06K 9/48* (2006.01)
*G06K 9/40* (2006.01)
*G21K 1/02* (2006.01)

(52) U.S. Cl.
USPC ........... 382/128; 382/129; 382/130; 382/131; 382/132; 382/168; 382/199; 382/254; 382/260; 382/266; 378/147

(58) Field of Classification Search
CPC ............. G06K 9/00; H05G 1/64; G21K 1/02
USPC ................... 382/128–132; 378/98.12, 147
See application file for complete search history.

(56) References Cited

U.S. PATENT DOCUMENTS

| | | | |
|---|---|---|---|
| 5,506,913 A * | 4/1996 | Ibison et al. | 382/132 |
| 5,901,240 A * | 5/1999 | Luo et al. | 382/132 |
| 6,212,291 B1 * | 4/2001 | Wang et al. | 382/132 |
| 6,356,651 B2 * | 3/2002 | Murakami | 382/128 |
| 6,577,701 B2 | 6/2003 | Ukita et al. | |
| 6,775,399 B1 * | 8/2004 | Jiang | 382/128 |
| 7,016,458 B2 | 3/2006 | Francke | |

(Continued)

OTHER PUBLICATIONS

Lehmann et al., "Automatic localization and delineation of collimation fields in digital and film-based radiographs", Medical Imaging 2002: Image Processing, SPIE Proceedings vol. 4684, pp. 1215-1223.*

(Continued)

*Primary Examiner* — Matthew Bella
*Assistant Examiner* — Jose M Torres
(74) *Attorney, Agent, or Firm* — Vista IP Law Group, LLP

(57) ABSTRACT

A process for detecting the edges of collimator blades in digital radiography images in the first pass detects the edges of the collimator blades using original image, and the in the second pass repeats edge detection using an image enhanced by a histogram matching technique, for example. The edge detection using an enhanced image may also be repeated any number of times in cases of complex anatomy or when selected radiographic techniques does do not provide sufficient imaging data. The results of the second pass, or the collection of the results of multiple second passes, are then combined with the result from the first pass to form a list of the potential blade edge candidates. A desirable number of edges are then selected from the combined list to form a polygon which encloses the target area of the image, thereby providing the shutter area.

19 Claims, 3 Drawing Sheets

(56) References Cited

U.S. PATENT DOCUMENTS

| | | | |
|---|---|---|---|
| 7,499,575 B2* | 3/2009 | Bohm et al. | 382/128 |
| 2004/0068167 A1 | 4/2004 | Hsieh et al. | |
| 2006/0052690 A1 | 3/2006 | Sirohey et al. | |
| 2008/0069470 A1* | 3/2008 | Yu et al. | 382/266 |

OTHER PUBLICATIONS

Behiels et al., "Restrospective correction of the heel effect in hand radiographs", Medical Image Analysis 6, 2002, pp. 183-190.*

Kawashita et al., "Collimation Detection in Digital Radiographs Using Plane Detection Hough Transform", Lectures in Computer Science, 2003, vol. 2774, pp. 394-401.*

International Search Report dated Sep. 14, 2009 for PCT Patent Application No. PCT/US2009/039168.

Written Opinion dated Sep. 14, 2009 for PCT Patent Application No. PCT/US2009/039168.

International Preliminary Report on Patentability dated Oct. 5, 2010 for PCT Patent Application No. PCT/US2009/039168.

* cited by examiner

MULTI-PASS EDGE DETECTION OF COLLIMATOR BLADES IN DIGITAL RADIOGRAPHY IMAGES

CROSS-REFERENCE TO RELATED APPLICATIONS

The present application claims priority to U.S. provisional Application No. 61/041,266, filed on Apr. 1, 2008.

BACKGROUND OF THE INVENTION

1. Field of the Invention

The present invention relates to digital radiography and, more specifically, to a method for the detection of collimator blades in digital radiography images.

2. Description of the Related Art

An essential step in processing digital radiography images is to detect the collimator blades. The information obtained from the detection of the collimator blades is then used to determine the area enclosed by the blades, and the statistics associated with the image within this area are calculated for use in subsequent image processing steps. The portion of image that is outside the area of the collimator blades may then be discarded to facilitate only useful image data storage, transmission and processing.

This technique of identifying the target area and discarded undesired areas is commonly referred to as the Auto Shutter process. The area enclosed by the collimator blades is referred to as the shutter area. The typical Auto Shutter process comprises the two steps: (1) the use of edge detection algorithms, such as the Hough transform, to detect the potential edges of the collimator blades in the image, which appear as straight lines; and (2) the selection of desirable edges. Unfortunately, the Hough transform is often unable to detect all the desirable edges because some or all of the collimator blade edges may be too weak for successful detection. As a result, an erroneous area may be selected and the diagnostic quality of image will therefore be compromised.

BRIEF SUMMARY OF THE INVENTION

It is therefore a principal object and advantage of the present invention to provide a method for more accurately detecting collimator blade edges.

It is an additional object and advantage of the present invention to provide a method for improving diagnostic image quality.

It is a further object and advantage of the present invention to provide a method for improving useful image data storage, transmission and processing.

In accordance with the foregoing objects and advantages, the present invention provides a process for detecting the edges of collimator blades in a digital radiography image that comprises at least two passes for improved edge detection and location of a target area in the image. The first pass in the process is to use the captured image (i.e., original image) to detect the edges of the collimator blades. This pass may be performed by implementing conventional edge detection processes and algorithms, such as the Hough transform. The second pass in the process is to repeat edge detection using an enhancing image. Image enhancement may be accomplished by using a histogram matching technique. This pass may also be repeated any number of times in cases of complex anatomy or when selected radiographic techniques do not provide sufficient imaging data. The results of the second pass, or the collection of the results of multiple second passes, are then combined with the result from the first pass to form a list of the potential blade edge candidates. A desirable number of edges are then selected from the combined list to form a polygon which encloses the target area of the image, thereby providing the shutter area.

BRIEF DESCRIPTION OF THE SEVERAL VIEWS OF THE DRAWING

The present invention will be more fully understood and appreciated by reading the following Detailed Description in conjunction with the accompanying drawing, in which.

DETAILED DESCRIPTION OF THE INVENTION

Figure 1:
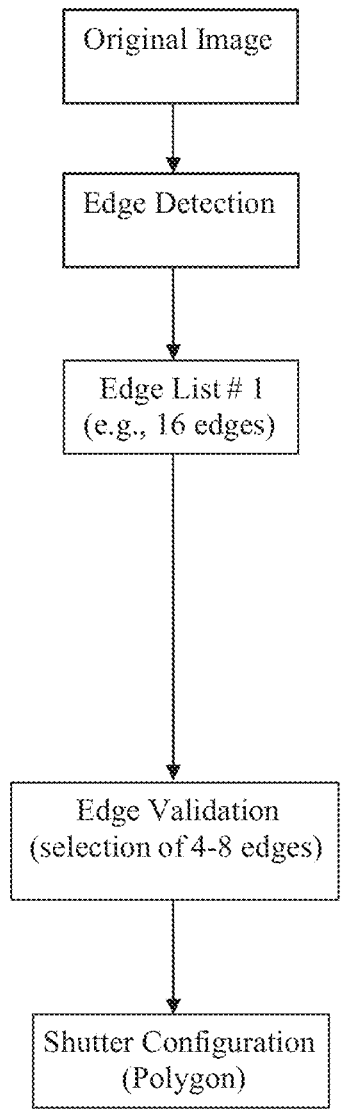
FIG. 1 is a flowchart of a prior art method for the detection of collimator blades in digital radiography images.

Referring now to the drawings, wherein like reference numerals refer to like parts throughout, there is seen in FIG. 1 a conventional method for detecting collimator blades. In the conventional method, an original image is processed using edge detection to detect a list of potential edges of collimator blades in the image, which appear as straight lines. A sample number of edges, such as four to eight, and then selected and used to determine the shutter configuration.

Figure 2:
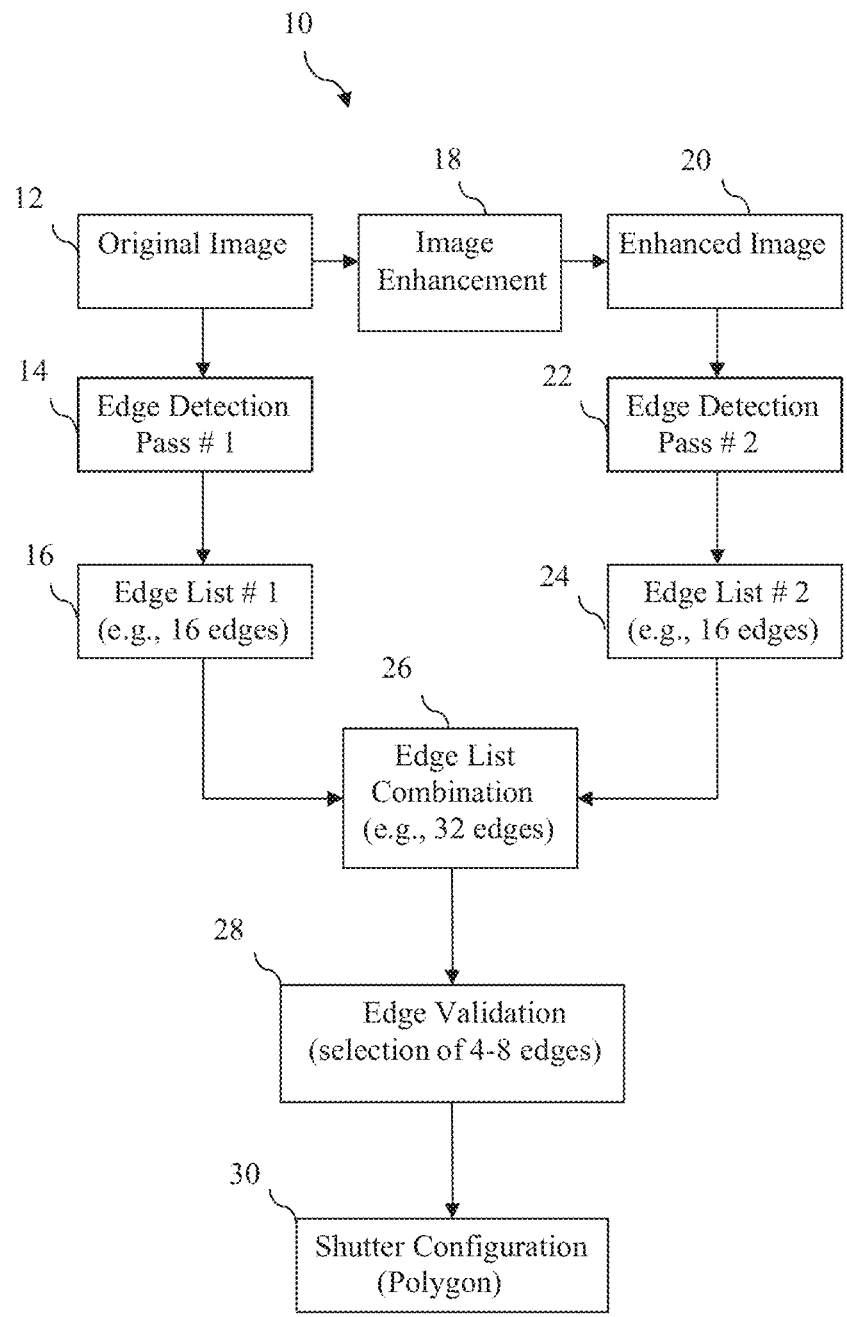
FIG. 2 is a flowchart of a method for the detection of collimator blades in digital radiography images according to the present invention.

Referring to FIG. 2, there is seen a method 10 for detecting the collimator blade edges in the digital radiography image according to the present invention. Method 10 begins with the original image 12. Image 12 is analyzed in a first edge detection pass 14 to detect the edges of any collimator blades within the image. Referring to FIG. 2, step 14 may be performed by implementing conventional edge detection algorithms, such as the Hough transform, on the digital image. The detected edges are then stored in first edge list 16.

The original image 12 is enhanced 18 resulting in an enhanced image 20. This enhanced image is analyzed in a second edge detection pass 22. The detected edges are stored in a second edge list 24.

The edges in first edge list 16 and second edge list 24 are combined to form a combined edge list 26. All the edges in the combined edge list 26 are then validated 28, and a predetermined or desirable number of edges are selected as representing the collimator blades. Finally, a polygon is drawn 30 to enclose the shutter area.

In method 10, as seen in FIG. 2, the left branch containing first edge detection pass 16 has the same functionality as the counterpart in the conventional method, as seen in FIG. 1. However, the right branch of method 10 containing second edge detection pass 22 is designed particularly to detect weak edges in the enhanced image. This processing may be repeated any number of times in cases of complex anatomy or when selected radiographic techniques does do not provide sufficient imaging data.

Image enhancement 18 is accomplished using the histogram matching technique. In brief, the enhanced image is generated by modifying the pixel values of the original image in such a way that the histogram of the original image ("source histogram") is modified to match the "destination histogram" of the enhanced image. The "destination histogram" is so designed as to raise weak edges in the image.

Figure 3:
FIG. 3 is a image processed according to the present invention.

There is seen in FIG. 3 an enhanced image 20 including a polygon 32 to enclose the shutter area 34.

It should be recognized by those of skill in the art that once the shutter area 30 is defined, the image may be cropped or otherwise handled according to conventional methods or devices, such as data storage, transmission and processing.

What is claimed is:

1. A method for detecting collimator blade edges in a digital radiography image, comprising:
   performing a first detection pass of said image to generate a first list of detected edges;
   enhancing said image;
   performing a second detection pass of said enhanced image to generate a second list of detected edges;
   combining said first list and said second list to generate a combined edge list;
   validating a plurality of the detected edges in said combined edge list; and
   selecting a predetermined number of validated edges.

2. The method of claim 1, wherein the act of enhancing the image comprises modifying pixel values of said image according to a predetermined histogram transformation.

3. The method of claim 2, wherein said first list of detected edges and said second list of detected edges are stored in memory prior to said act of combining said first list and second list to generate the combined edge list.

4. The method of claim 1, wherein said predetermined number of validated edges comprises four to eight.

5. The method of claim 1, wherein the act of performing the second detection pass and the act of combining are repeated at least once.

6. The method of claim 1, wherein said first detection pass is accomplished using a Hough transform.

7. The method of claim 1, further comprising enclosing a shutter area in said image by providing a polygon based on the predetermined number of validated edges.

8. A non-transitory computer readable medium including program instructions for detecting collimator blade edges in a digital radiography image which when executed perform a method comprising:
   performing a first detection pass of said image to generate a first list of detected edges;
   enhancing said image;
   performing a second detection pass of said enhanced image to generate a second list of detected edges;
   combining said first list and said second list to generate a combined edge list;
   validating a plurality of the detected edges in said combined edge list; and
   selecting a predetermined number of validated edges.

9. The computer readable medium of claim 8, wherein said act of performing said first detection pass comprises using a Hough transform.

10. The computer readable medium of claim 9, further comprising performing a third detection pass to generate a third list of detected edges.

11. The computer readable medium of claim 8, wherein said predetermined number of validated edges comprises four to eight.

12. The computer readable medium of claim 8, wherein said act of enhancing said image comprises modifying pixel values of said image according to a predetermined histogram transformation.

13. An apparatus for detecting collimator blade edges in a digital radiography image, comprising:
   a processing unit configured for:
      performing a first detection pass of said image to generate a first list of detected edges;
      enhancing said image;
      performing a second detection pass of said enhanced image to generate a second list of detected edges;
      combining said first list and said second list to generate a combined edge list; and
      validating a plurality of the detected edges in said combined edge list.

14. The apparatus of claim 13, wherein the processing unit is configured to enhance the image by modifying pixel values of the image according to a predetermined histogram transformation.

15. The apparatus of claim 14, further comprising a memory for storing the first list of detected edges and the second list of detected edges.

16. The apparatus of claim 13, wherein the processing unit is further configured for selecting a predetermined number of validated edges.

17. The apparatus of claim 13, wherein the processing unit is configured to repeat the act of performing the second detection pass and the act of combining at least once.

18. The apparatus of claim 13, wherein the processing unit is configured to perform the first detection pass using a Hough transform.

19. The apparatus of claim 13, wherein the processing unit is further configured for enclosing a shutter area in the image by providing a polygon based on a predetermined number of validated edges.

* * * * *